United States Patent
Bristow

(10) Patent No.: US 10,071,942 B2
(45) Date of Patent: Sep. 11, 2018

(54) PROCESS FOR THE PRODUCTION OF DIMETHYL ETHER FROM GASEOUS MIXTURES OF CARBON MONOXIDE, HYDROGEN AND METHYL ACETATE

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 15/312,107

(22) PCT Filed: Jun. 12, 2015

(86) PCT No.: PCT/EP2015/063153
§ 371 (c)(1),
(2) Date: Nov. 17, 2016

(87) PCT Pub. No.: WO2015/193186
PCT Pub. Date: Dec. 23, 2015

(65) Prior Publication Data
US 2017/0088495 A1    Mar. 30, 2017

(30) Foreign Application Priority Data

Jun. 20, 2014 (EP) .................................. 14173351

(51) Int. Cl.
| | |
|---|---|
| *C07C 41/09* | (2006.01) |
| *C07C 41/16* | (2006.01) |
| *C07C 51/09* | (2006.01) |
| *C07C 29/151* | (2006.01) |
| *C07C 67/37* | (2006.01) |
| *C10K 1/16* | (2006.01) |

(52) U.S. Cl.
CPC .......... *C07C 41/09* (2013.01); *C07C 29/1518* (2013.01); *C07C 41/16* (2013.01); *C07C 51/09* (2013.01); *C07C 67/37* (2013.01); *C10K 1/16* (2013.01); *Y02P 20/142* (2015.11)

(58) Field of Classification Search
CPC ..... C07C 41/09; C07C 51/09; C07C 29/1518; C07C 67/37
See application file for complete search history.

(56) References Cited

U.S. PATENT DOCUMENTS

| | | |
|---|---|---|
| 3,186,145 A | 6/1965 | Pelton et al. |
| 4,050,909 A | 9/1977 | Ranke |

FOREIGN PATENT DOCUMENTS

| | | |
|---|---|---|
| EP | 2 292 578 A1 | 3/2011 |
| GB | 2 253 623 A | 9/1992 |
| WO | WO 96/28408 A1 | 9/1996 |
| WO | WO9921814 A1 * | 5/1999 |
| WO | WO 2011/027105 A1 | 3/2011 |

* cited by examiner

*Primary Examiner* — Paul A Zucker
(74) *Attorney, Agent, or Firm* — Nixon & Vanderhye P.C.

(57) ABSTRACT

Process for producing dimethyl ether from gaseous mixtures of CO, $H_2$ and methyl acetate (MeOAc) contaminant by contacting a gaseous mixture of CO, $H_2$ and MeOAc contaminant in a first scrubbing zone with methanol to recover a scrubbed gaseous mixture depleted in MeOAc and a used methanol stream containing MeOAc. The scrubbed gaseous mixture is contacted in a second scrubbing zone with methanol to recover a scrubbed gaseous mixture further depleted in MeOAc and a second used methanol stream containing no or a reduced amount of MeOAc compared to the first used methanol stream. A portion of the second used methanol stream is dehydrated in the presence of a catalyst to produce a crude dehydration reaction product containing dimethyl ether, unconverted methanol and water. A water stream is recovered from the crude dehydration product containing water and 3 mol % or less acetic acid and a dimethyl ether stream.

22 Claims, 1 Drawing Sheet

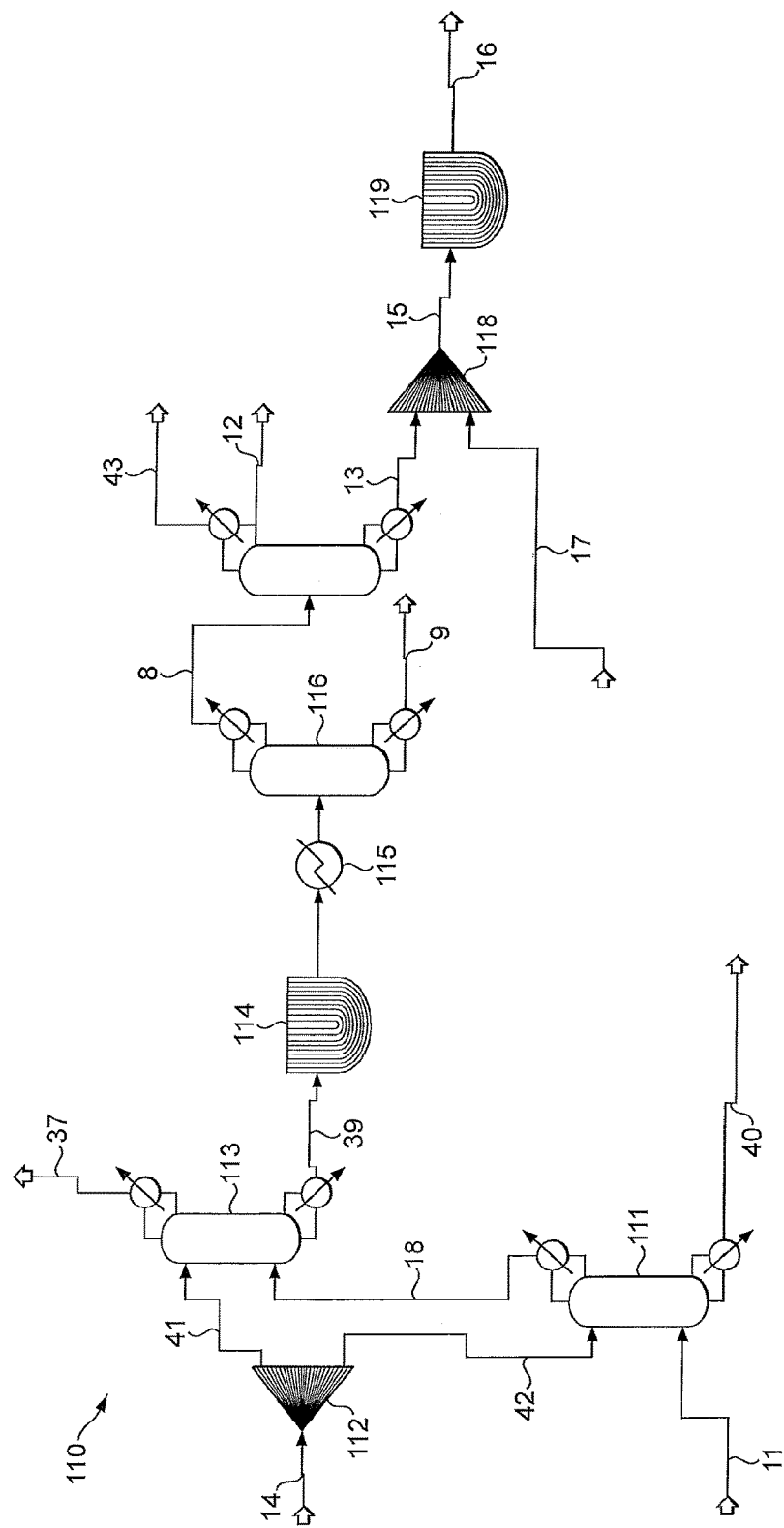

PROCESS FOR THE PRODUCTION OF DIMETHYL ETHER FROM GASEOUS MIXTURES OF CARBON MONOXIDE, HYDROGEN AND METHYL ACETATE

This application is the U.S. national phase of International Application No. PCT/EP2015/063153 filed Jun. 12, 2015 which designated the U.S. and claims priority to European Patent Application No. 14173351.9 filed Jun. 20, 2014, the entire contents of each of which are hereby incorporated by reference.

The present invention relates to producing purified water streams in processes for the production of dimethyl ether from gaseous mixtures of carbon monoxide and hydrogen contaminated with methyl acetate and in particular producing purified water streams from gaseous mixtures of carbon monoxide and hydrogen contaminated with methyl acetate in processes for the co-production of acetic acid and dimethyl ether from methanol and methyl acetate.

BACKGROUND OF THE INVENTION

WO 96/248408 describes a process for the production and recovery of dimethyl ether by dehydration of methanol which reduces the distillation duties associated with the preparation of fresh methanol feedstock and/or recovery of unconverted methanol for use as recycle feedstock to the dimethyl ether production process while maintaining a high rate of conversion of methanol to dimethyl ether.

GB 2253623 describes a process for the production of dimethyl ether by feeding synthesis gas in a reactor with a catalyst composition and withdrawing a dimethyl ether-containing effluent wherein carbon dioxide obtained from the reactor effluent is recycled to the reactor.

Processes for the co-production of acetic acid and dimethyl ether may be carried out by catalytic dehydration and hydrolysis of mixtures of methanol and methyl acetate. Such co-production processes are known from, for example WO 2011/027105. WO 2011/027105 describes processes for the co-production of acetic acid and dimethyl ether by contacting methanol and methyl acetate with a catalyst composition at a temperature in the range 140 to 250 C which catalyst composition comprises a zeolite having a 2-dimensional channel system comprising at least one channel which has a 10-membered ring.

In such dehydration-hydrolysis processes methanol is dehydrated to dimethyl ether and methyl acetate is hydrolysed to acetic acid. The reactions can be represented by:

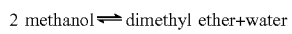
2 methanol ⇌ dimethyl ether+water

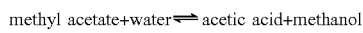
methyl acetate+water ⇌ acetic acid+methanol

These reactions are equilibrium limited. The hydrolysis reaction consumes water and produces methanol and the dehydration reaction consumes methanol and produces water.

It has now been found that in the presence of solid acid catalysts, such as zeolites, the dehydration reaction is relatively slow and since water is consumed more quickly by the hydrolysis reaction, it is typically necessary to provide water to the system to maintain a steady-state concentration of water in the reaction. Water may be added to the process through process streams such as feed and recycle streams to the dehydration-hydrolysis process.

In general, methanol obtained by commercial synthesis processes contains water and may also contain some dimethyl ether. The amount of water present in produced methanol can vary depending upon such factors as the specific process operating conditions used in the process and the composition of the feed to the methanol synthesis process, and in particular the amount of carbon dioxide employed.

Thus the amount of water present in feeds, particularly in methanol feeds, to dehydration-hydrolysis processes may be sub-optimal for maintaining or optimising the operation of such processes. Furthermore, if such processes are operated as continuous processes, recycling of water-containing streams to the process can cause or contribute to fluctuations in the water concentration within the process.

In commercial chemical processes, process streams for disposal, such as process water streams, comprise or are treated so as to comprise acceptable levels of organic contaminants prior to their disposal. For example, the presence of acetic acid in process water streams for disposal can be problematic. Simple distillation processes can be successfully employed to reduce the concentration of acetic acid in water to about 3 mol % acetic acid but are not effective to reduce the concentration of acetic acid further. Additional processing to meet the demands of economic and/or environment considerations can be employed to reduce the acetic acid concentration to acceptable levels but additional processing, for example by reverse osmosis techniques, is likely to result in a loss of process value and/or higher process operating costs.

SUMMARY OF THE INVENTION

Thus, there is a need for the provision of process water streams which contain sufficiently low levels of acetic acid that additional processing treatment of the produced water is eliminated or mitigated. In particular, there is a need for a process for the co-production of acetic acid and dimethyl ether from methanol and methyl acetate feed stocks in which the amount of water supplied to the co-production process can be controlled and wherein process water streams generated in or in connection with the process contain sufficiently low levels of acetic acid that additional processing treatment of the produced water is eliminated or mitigated. Furthermore, there is a need to treat process water streams generated by the dehydration of methanol feed stock, which methanol feed stock is derived from gaseous mixtures comprising carbon oxide(s) and hydrogen and which methanol feed stock also comprises methyl acetate as a contaminant and, in particular methanol feed stocks derived from gaseous mixtures comprising carbon oxide(s) and hydrogen and methyl acetate contaminant recovered from crude carbonylation product streams produced by carbonylating dimethyl ether with a carbon monoxide-containing gas in the presence of a carbonylation catalyst.

Accordingly, the present invention provides a process for the production of dimethyl ether from gaseous mixtures of carbon monoxide, hydrogen and methyl acetate contaminant which process comprises:

contacting a gaseous mixture of carbon monoxide, hydrogen and methyl acetate contaminant in a first scrubbing zone with a first portion of methanol to recover a scrubbed gaseous mixture depleted in methyl acetate and a first used methanol stream containing methyl acetate;

contacting the scrubbed gaseous mixture in a second scrubbing zone with a second portion of methanol to recover a scrubbed gaseous mixture further depleted in methyl acetate and a second used methanol stream containing no methyl acetate or a reduced amount of methyl acetate compared to the first used methanol stream;

dehydrating at least a portion of the second used methanol stream in the presence of at least one catalyst to produce a crude dehydration reaction product comprising dimethyl ether, unconverted methanol and water;

recovering from the crude dehydration product a water stream comprising mainly water and 3 mol % or less acetic acid and a dimethyl ether stream.

The present invention further provides a process for the co-production of acetic acid and dimethyl ether by dehydration-hydrolysis of methanol and methyl acetate which process comprises:

contacting a gaseous mixture of carbon monoxide, hydrogen and methyl acetate contaminant in a first scrubbing zone with a first portion of methanol to recover a scrubbed gaseous mixture depleted in methyl acetate and a first used methanol stream containing methyl acetate;

contacting the scrubbed gaseous mixture in a second scrubbing zone with a second portion of methanol to recover a scrubbed gaseous mixture further depleted in methyl acetate and a second used methanol stream containing no methyl acetate or a reduced amount of methyl acetate compared to the first used methanol stream;

dehydrating at least a portion of the second used methanol stream in the presence of at least one catalyst to produce a crude dehydration reaction product comprising dimethyl ether, unconverted methanol and water;

recovering from the crude dehydration product a water stream comprising mainly water and 3 mol % or less acetic acid and a dimethyl ether stream comprising dimethyl ether and methanol;

separating dimethyl ether from the dimethyl ether stream to produce a methanol stream comprising methanol and water; and contacting the methanol stream or a part thereof, methyl acetate and optionally one or more recycle streams comprising one or more of methanol, methyl acetate and water in the presence of at least one catalyst to generate a dehydration-hydrolysis reaction product comprising dimethyl ether and acetic acid.

In one or all embodiments of the present invention, the gaseous mixture of carbon monoxide, hydrogen and methyl acetate contaminant contacted in the first scrubbing zone with the first portion of methanol is a gaseous mixture recovered from a crude carbonylation product comprising methyl acetate, unreacted carbon monoxide and hydrogen, suitably a crude carbonylation product produced by carbonylating dimethyl ether with a carbon monoxide-containing gas in the presence of a carbonylation catalyst, preferably a zeolite catalyst and hydrogen. The carbon monoxide-containing gas may comprise carbon dioxide.

Thus, the present invention yet further provides an integrated process for the co-production of acetic acid and dimethyl ether by dehydration-hydrolysis of methanol and methyl acetate which process comprises carbonylating dimethyl ether with carbon monoxide in the presence of a carbonylation catalyst and hydrogen and optionally carbon dioxide to produce a crude carbonylation product comprising methyl acetate, unreacted carbon monoxide and hydrogen;

recovering from the crude carbonylation reaction product a stream comprising the majority of the methyl acetate and a stream of a gaseous mixture of carbon monoxide, hydrogen and methyl acetate contaminant;

contacting the gaseous mixture of carbon monoxide, hydrogen and methyl acetate contaminant or a part thereof in a first scrubbing zone with a first portion of methanol to recover a scrubbed gaseous mixture depleted in methyl acetate and a first used methanol stream containing methyl acetate;

contacting the scrubbed gaseous mixture in a second scrubbing zone with a second portion of methanol to recover a scrubbed gaseous mixture further depleted in methyl acetate and a second used methanol stream containing no methyl acetate or a reduced amount of methyl acetate compared to the first used methanol stream;

dehydrating at least a portion of the second used methanol stream in the presence of at least one catalyst to produce a crude dehydration reaction product comprising dimethyl ether, unconverted methanol and water;

recovering from the crude dehydration product a water stream comprising mainly water and 3 mol % or less acetic acid and a dimethyl ether stream comprising dimethyl ether, and methanol;

separating dimethyl ether from the dimethyl ether stream to produce a methanol stream comprising methanol and water; and contacting the methanol stream or a part thereof, methyl acetate and optionally one or more recycle streams comprising one or more of methanol, methyl acetate and water in the presence of at least one catalyst to generate a dehydration-hydrolysis reaction product comprising dimethyl ether and acetic acid.

In some or all embodiments of the present invention, methyl acetate supplied to the dehydration-hydrolysis process is recovered from a process for the carbonylation of dimethyl ether with a carbon monoxide-containing gas, in the presence of a carbonylation catalyst, preferably a zeolite catalyst. Suitably, the carbon monoxide-containing gas comprises one or both of hydrogen and carbon dioxide.

In some or all embodiments of the present invention, the process further comprises recovering from the dehydration-hydrolysis reaction product, an acetic acid-rich stream and a dimethyl ether-rich stream, for example by distillation methods, such as by fractional distillation, in one or more distillation columns.

In some or all embodiments of the present invention, a water stream comprising mainly water, preferably at least 95 mol % water, more preferably at least 99 mol % water and 0 to 0.1 mol % acetic acid is recovered from the crude dehydration product.

Advantageously, the process of the present invention allows the amount of water introduced into the dehydration-hydrolysis process to be controlled by utilising a separate dehydration step upstream of the dehydration-hydrolysis process from which dehydration step process streams containing varying amounts of water are removed dependent upon the water requirements of the dehydration-hydrolysis reaction to maintain effective operation thereof.

More advantageously, the process of the present invention allows water streams removed from the dehydration step to be sufficiently pure and devoid of acetic acid that additional treatment to reduce their acetic acid content is eliminated or at least mitigated.

Furthermore, the present invention provides for enhanced production of dimethyl ether which may be utilised subsequently as a feedstock in other chemical processes, and in particular as a feedstock to carbonylation processes for the production of methyl acetate.

BRIEF DESCRIPTION OF THE DRAWING

The invention is further described with reference to the accompanying drawing which is a schematic diagram illustrating embodiments of the present invention for the co-production of acetic acid and dimethyl ether incorporating two-stage scrubbing of gaseous mixtures of carbon monoxide, hydrogen and methyl acetate with methanol.

DETAILED DESCRIPTION OF THE INVENTION

Suitably, the gaseous mixture comprising carbon monoxide, hydrogen and methyl acetate provided to the first scrubbing zone further comprises carbon dioxide.

Suitably, a gaseous mixture provided to the first scrubbing zone may comprise methyl acetate in an amount of about >0 to 5 mol %.

Suitably, a gaseous mixture provided to the first scrubbing zone comprises carbon monoxide, hydrogen and carbon dioxide and methyl acetate in an amount of about >0 to 5 mol %.

Preferably, at least 90% and more preferably at least 99% of the methyl acetate present in the gaseous mixture is removed by contact with the first and second portions of methanol. Thus, suitably a gaseous mixture after contact with the second portion of methanol comprises methyl acetate in an amount of 0 to 1 mol %, preferably, 0 to 0.1 mol %.

Scrubbing of the gaseous mixture is conducted in a first scrubbing zone by contacting it with a first portion of methanol to produce a gaseous mixture depleted in methyl acetate content as compared to the gaseous mixture prior to scrubbing. The scrubbed gaseous mixture is subjected to a second scrubbing by contacting it in a second scrubbing zone with a second portion of methanol. Desirably, scrubbing is performed by counter-current contact of the gaseous mixture and liquid methanol so that the gaseous mixture will flow upwardly through a scrubbing zone and methanol will flow downwardly through the same scrubbing zone.

Each of the scrubbing zones may be of conventional design, for example a column within which high surface area materials, such as trays or packing, is arranged so as to enable intimate contact of the gaseous mixture and methanol and to ensure good mass transfer between gas and liquid phases. Conventional trays and packing materials such as metal helices, Raschig rings and the like may be suitably employed.

In one or more embodiments of the present invention one or both of the first and second scrubbing zones contains 3 to 10 theoretical stages.

The first and second scrubbing zones are arranged in series. Each of the first and second scrubbing zones may be a stand-alone unit. Alternatively, the first and second scrubbing zones may be housed within a single scrubbing unit.

In one or more embodiments of the present invention, the first and second scrubbing zones are integrated within a single scrubbing column, preferably in which the second scrubbing zone is located in an upper portion of the column and the first scrubbing zone is located within the lower portion of the column such that the gaseous mixture comprising carbon monoxide, hydrogen and methyl acetate passes upwardly through the first scrubbing zone and is brought into contact therein with the first methanol portion and a scrubbed gas depleted in methyl acetate passes upwardly from the first scrubbing zone into the second scrubbing zone and contacted therein with the second portion of methanol and the scrubbed gas further depleted in methyl acetate is withdrawn from the second scrubbing zone of the scrubbing column, suitably as an overhead stream from the column; a first used methanol stream is recovered from the first scrubbing zone of the column and a second used methanol stream is recovered from the second scrubbing zone. Preferably, the second portion of methanol is introduced into the second scrubbing zone at a point at or near to the top of the column and the second used methanol stream is recovered from the second scrubbing zone at a point above the feed point of the first portion of methanol to the column.

Each of the first and second scrubbing zones may be operated at any suitable pressure and temperature. In general, scrubbing efficiency is improved with decreased temperature and increased pressure. Suitably, a scrubbing zone is operated at a pressure in the range of about 50 to 90 barg and a methanol inlet temperature of from about −50° C. to 100° C., for example 0° C. to 60 C, such as 35° C. to 55° C.

Suitably, one or both of the first and second portions of methanol may be pure methanol or a methanol-rich mixture, suitably a methanol-rich mixture comprising one or both of water and dimethyl ether. Mixtures of methanol and one or both of water and dimethyl ether may comprise methanol in an amount of 50 mol % or greater, for example in an amount 50 to 99 mol %, preferably in an amount of 80 mol % or greater. Water may be present in a mixture in an amount 0 mol % to 35 mol %, for example 5 to 20 mol %. Dimethyl ether may be present in a mixture in an amount of 0 to 10 mol %.

The composition of the first portion of methanol may be the same or different to that of the composition of the second portion of methanol, preferably the same.

In one or more embodiments of the present invention, the first and second portions of methanol each comprise a mixture of methanol, water and dimethyl ether and wherein water and dimethyl ether are present in the mixture in a total amount of >0 to 35 mol %.

The amount of methanol supplied as the first methanol portion to the first scrubbing zone can vary but is preferably selected so as to remove most of the methyl acetate present in the gaseous mixture, for example so as to remove 50 to <100 mol %, preferably 90 to <100 mol % methyl acetate present in the gaseous mixture. Suitably, the ratio of the amount of the first portion of methanol to the amount of the second portion of methanol is in the range 1:5 to 1:15, for example 1:10.

In one or more embodiments of the present invention, the first and second portions of methanol comprise mixtures of methanol and up to a total of 20 mol % of water and dimethyl ether and the ratio of the amount of a first portion of methanol to the amount of the second portion of methanol is 1:5 to 1:15, for example 1:10.

The second portion of methanol scrubs the gaseous mixture from the first scrubbing zone and removes all or substantially all of the methyl acetate remaining in the gaseous mixture. Suitably, the second used methanol stream comprises 0 to 0.1 mol % methyl acetate but higher amounts of methyl acetate may be tolerated such as 0 to 0.5 mol % methyl acetate, for example 0 to 0.3 mol % methyl acetate.

Desirably, the first and second portions of methanol are provided from a single methanol feed supply, preferably the single methanol feed is split into the first and second portions so as to provide a major amount of methanol to the second scrubbing zone and a minor amount of methanol to the first scrubbing zone. Preferably, the methanol feed is split so as to provide a ratio of the amount of the first portion of methanol to the amount of the second portion of methanol in the range 1:5 to 1:15, for example 1:10.

In one or all embodiments of the present invention, the first and second portions of methanol are fed to the first and second scrubbing zones respectively within a single scrubbing column and the first and second methanol portions are provided from a single methanol feed. Preferably, the second portion of methanol is supplied to the second scrubbing zone at a point at or near to the top of the column. Desirably, the second used methanol stream withdrawn from the second scrubbing zone comprises the majority of the methanol fed to the column. Preferably, the second used methanol stream comprises 50% or more, such as 80% or more, preferably 90% or more of the total methanol feed to the column.

In one or all embodiments of the present invention there is provided a process which comprises contacting the gaseous mixture of carbon monoxide, hydrogen and methyl acetate contaminant in a first scrubbing zone with a first portion of methanol to recover a scrubbed gaseous mixture depleted in methyl acetate and a first used methanol stream containing methyl acetate; contacting the scrubbed gaseous mixture in a second scrubbing zone with a second portion of methanol to recover a scrubbed gaseous mixture further depleted in methyl acetate and a second used methanol stream containing no methyl acetate or a reduced amount of methyl acetate compared to the first used methanol stream; and wherein the first and second scrubbing zones are integrated within a single scrubbing column, the first scrubbing zone of which is the lower scrubbing zone within the column and located below the second scrubbing zone which second scrubbing zone is the upper scrubbing zone within the column. Suitably, in these embodiments, the first used methanol stream is recovered from the first scrubbing zone of the column. Suitably, the first used methanol stream is withdrawn from the bottom of the column at or near to the feed point of the gaseous mixture to the column. The gaseous mixture scrubbed with the first portion of methanol and depleted in methyl acetate flows upwardly through the column and is subjected in the second scrubbing zone to a second scrubbing with a second portion of methanol to reduce the methyl acetate content of the gaseous mixture still further. Preferably, the second portion of methanol is introduced into the column at or near to the top of the second scrubbing zone and suitably the second used methanol stream containing absorbed methyl acetate is recovered from the second scrubbing zone at a point above the feed point of the first portion of methanol to the column. Suitably, the first and second portions of methanol fed to the column are provided from a single feed of methanol. Suitably, the single methanol feed comprises a mixture of methanol and up to a combined total of 20 mol % of water and dimethyl ether. Suitably, the single methanol feed is split to provide a major amount of methanol to the second scrubbing zone and a minor amount of methanol to the first scrubbing zone. Preferably, the methanol feed is split into a first and second methanol portions to provide a ratio of the amount of the first portion of methanol to the amount of the second portion of methanol in the range 1:5 to 1:15, for example 1:10. Preferably, the amount of methanol supplied as the first methanol portion is sufficient to remove most of the methyl acetate present in the gaseous mixture, for example to remove 50 to <100%, preferably 90 to <100% methyl acetate present in the gaseous mixture. Preferably, the second used methanol stream recovered from the second scrubbing zone comprises the majority of the methanol feed to the column, for example the second used methanol stream may comprise 50% or more, such as 80% or more, preferably 90% or more of the total methanol feed to the column. Desirably, the second used methanol stream comprises 0 to 0.1 mol % methyl acetate but higher amounts may be tolerated, for example 0 to 0.5 mol % methyl acetate, such as 0 to 0.3 mol % methyl acetate.

In some or all embodiments of the present invention the second used methanol stream comprises 50 to 99 mol % methanol, such as 80 to 90 mol % methanol, >0 to 35 mol % water, such as 5 to 20 mol % water and 0 to 10 mol % dimethyl ether and 0 to 1 mol %, such as 0 to 0.5 mol % methyl acetate, for example 0 to 0.1 mol % methyl acetate.

In a preferred embodiment, the second portion of methanol comprises water and dimethyl ether and the second used methanol stream comprises methanol, water and dimethyl ether and methyl acetate, preferably methyl acetate in an amount of 0 to 1 mol %, such as 0 to 0.5 mol %, preferably 0 to 0.1 mol %. Desirably, the second used methanol stream comprises water and dimethyl ether in a total amount of 0 to 20 mol % and methyl acetate in an amount of 0 to 1 mol %, such as 0 to 0.5 mol %, preferably in an amount 0 to 0.1 mol %.

If water is present in the second used methanol stream, small quantities of acetic acid may be generated therein by the hydrolysis of methyl acetate present in the methanol stream.

The second used methanol stream or a portion thereof is dehydrated in the presence of at least one catalyst to produce a crude dehydration product comprising dimethyl ether, unconverted methanol and water.

Dehydration of the methanol stream may be carried out in the presence of any suitable catalyst which is effective to dehydrate methanol to form dimethyl ether and water. Useful catalysts include solid acid catalysts including aluminas such as gamma-alumina and fluorinated alumina, acidic zirconias, aluminium phosphate, silica-alumina supported tungsten oxides and solid Brønsted acid catalysts such as heteropolyacids and salts thereof and aluminosilicate zeolites.

The term "heteropolyacid" as used herein and throughout this specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be usefully utilised in the present invention include the free acids such as silicotungstic acids, phosphotungstic acids and 12-tungstophosphoric acid ($H_3[PW_{12}O_{40}] \cdot xH_2O$); 12-molybdophosphoric acid ($H_3[PMo_{12}O_{40}] \cdot xH_2O$); 12-tungstosilicic acid ($H_4[SiW_{12}O_{40}] \cdot xH_2O$); 12-molybdosilicic acid ($H_4[SiMo_{12}O_{40}] \cdot xH_2O0$ and ammonium salts of heteropolyacids, such as ammonium salts of a phosphotungstic acid or a silicotungstic acid.

Particularly useful zeolites include those zeolites having a 2-dimensional or 3 dimensional channel system and possess at least one channel which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

Suitably, the zeolite further comprises at least one channel having an 8-membered ring. Non-limiting examples include zeolites of framework type selected from FER, HEU and MFS.

The three-letter codes such as 'FER' refer to the framework structure type of the zeolites using the nomenclature proposed by the International Zeolite Association. Information about structure codes and zeolites is available in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

A zeolite utilised in the dehydration process may be employed in an exchanged form. Exchanged forms of zeolites can be prepared by techniques such as ion-exchange and impregnation. These techniques are well-known and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite utilised in the dehydration process may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

The second used methanol stream may be dehydrated as a vapour or as a liquid, preferably as a vapour. If desired, if the methanol stream contains liquid components these liquid components may be volatilised, for example using a preheater.

Suitably, the dehydration process is conducted as a heterogeneous process, either in the liquid phase or in the vapour phase. Thus, in practising the invention, the second used methanol stream in the liquid and/or vapour phase is passed through or over a catalyst which is effective to dehydrate methanol to form dimethyl ether and water, preferably a solid acid catalyst. The dehydration process may be conducted in any suitable reactor such as adiabatic or cooled reactor types.

Suitably, the dehydration process is conducted at temperatures of from 100° C. to 350° C., for example 150 to 300° C., such as 200 to 300° C. However, and, in particular where an adiabatic type reactor is employed, the dehydration process may be conducted over a broader temperature range, for example at temperatures in the range 100 to 450° C.

Suitably, the dehydration process is conducted at atmospheric or at pressures greater than atmospheric.

In one or more embodiments of the present invention, the dehydration is conducted as a heterogeneous process in the liquid phase at temperatures of from 140° C. to 210° C. and preferably at a pressure which is sufficient to maintain product dimethyl ether in solution, such as at pressures of at least 40 barg, for example 40 to 100 barg (4000 to 10,000 kPa). In such cases, the dehydration process may be carried out at a liquid hourly space velocity (LHSV) is in the range 0.2 to 20 $h^{-1}$.

In one or more embodiments of the present invention, the dehydration process is conducted as a heterogeneous process in the vapour phase at temperatures of from 150° C. to 300° C., preferably at a pressure of atmospheric to 30 barg (atmospheric to 3000 kPa), for example 10 to 20 barg (1000 to 2000 kPa). In such cases, the dehydration process may be carried out at a gas hourly space velocity (GHSV) in the range 500 to 40,000 $h^{-1}$.

In one or more embodiments of the present invention, the dehydration process is carried out in the presence of at least one catalyst selected from gamma-aluminas and zeolites, for example zeolites of framework type FER and MFI and under operating conditions which are maintained such that the dehydration is conducted in the vapour phase, for example at a temperature of from 150° C. to 300° C. and at a pressure of atmospheric to 30 barg (atmospheric to 3000 kPa).

Dehydration of the second used methanol stream generates dimethyl ether and water to provide a crude dehydration product comprising dimethyl ether, water and unconverted methanol. Typically, a crude dehydration product comprises dimethyl ether, water, unconverted methanol and 0 to 0.1 mol % acetic acid.

Dehydration of methanol produces water in-situ as a result of which the crude dehydration product typically comprises a greater amount of water than is present in the feed methanol. In addition, some, but not all, methyl acetate present in the feed is hydrolysed to acetic acid.

A crude dehydration product may comprise up to about 45 mol % dimethyl ether, for example about 20 to 45 mol % dimethyl ether, >0 to 60 mol %, for example about 20 to 45 mol % water, about 10 to 60 mol % methanol and about 0 to 3 mol % acetic acid, preferably about 0 to 0.1 mol % acetic acid.

Recovery from the crude dehydration product of i) a water stream comprising mainly water and 0 to 3 mol % acetic acid and ii) a dimethyl ether stream comprising dimethyl ether, water and methanol can, in principle, be achieved by any conceivable method, however preference is given to distillation methods, for example fractional distillation.

In some or all embodiments of the present invention, the recovery of a water stream from the crude dehydration product is carried out by distillation methods, for example by fractional distillation, in one or more distillation columns.

In a typical configuration, a distillation column has at least 5, such as at least 10 theoretical stages, such as at least 15 theoretical stages. Since distillation zones may have differing efficiencies 15 theoretical stages may be equivalent to at least 25 actual stages with an efficiency of about 0.7 or at least 30 actual stages with an efficiency of about 0.5.

Suitably, the distillation column is operated at elevated pressure, such as at a pressure of about 0.5 barg (50 kPa) or more, such as about 5 barg to 30 barg (500 to 3000 kPa), for example about 5 to 20 barg (500 to 2000 kPa).

At operating pressures of about 5 barg to 30 barg (500 to 3000 kPa), the heads temperature is maintained at temperatures of 120 to 180° C.

Suitably, the distillation column may be a tray or packed column.

In one or more embodiments, the distillation column has at least 10 theoretical stages, such as at least 15 theoretical stages, for example 15 theoretical stages. Preferably in these embodiments the column is operated at a pressure of from 5 to 30 barg (500 to 3000 kPa) and at a heads temperature of from 120 to 180° C., for example at a pressure of 5 to 20 barg (500 to 2000 kPa) and at a heads temperature of from 120 to 165° C.

Advantageously, processing of methanol streams according to the present invention allows production of methanol streams which comprise no methyl acetate or very small quantities of methyl acetate and ultimately results in crude dehydration products which comprise no acetic acid or very small quantities of acetic acid. More advantageously, essentially pure water streams comprising no or trace levels of acetic acid can be easily separated from the crude dehydration product by simple distillation and, if desired, discarded from the process without necessitating complex or expensive separation techniques to reduce the acetic acid content of recovered water streams to acceptable levels.

In some or all embodiments of the present invention, a water stream recovered from the crude dehydration product comprises at least 90 mol % water, such as at least 95 mol % water, for example 90 to 99 mol % water and 0 to 3 mol % acetic acid, for example 0 to 1 mol % acetic acid, such as 0 to 0.1 mol % acetic acid.

In a preferred embodiment, the water stream comprises 0 to 1 mol % acetic acid, for example 0 to 0.5 mol % acetic acid, preferably 0 to 0.1 mol % acetic acid.

In a preferred embodiment, the water stream comprises at least 95 mol % water, more preferably at least 99 mol % water, and 0 to 1 mol % acetic acid, more preferably 0 to 0.1 mol % acetic acid.

The amount of water present in a water stream withdrawn from the distillation column in which the crude dehydration product is distilled can be adjusted dependent upon the amount of water desired to be supplied to the dehydration-hydrolysis process. The amount of water fed to a dehydration-hydrolysis process can be determined by compositional analysis, for example by gas chromatography, of streams supplied to the process. If the total amount of water to the dehydration-hydrolysis process is less than desired, the amount of water in the water stream exiting the distillation column may be decreased. Similarly, if the total amount of water to the dehydration-hydrolysis process is greater than desired, the amount of water in the water stream exiting the column may be increased.

Control of the amount of water present in the water stream withdrawn from the distillation column may be achieved by adjusting one or both of the reflux ratio to the column and the reboiler duty (boil-up ratio).

Suitably, a distillation column is operated with a return of liquid reflux to the head of the column at a reflux to heads ratio dependent upon such factors as the required overhead stream composition. A suitable reflux ratio may be in the range 0.05 to 1. Increasing the reflux ratio increases the flow rate of the water stream exiting the column.

The distillation column may be, and preferably is, equipped with a reboiler at the base of the column. The reboiler may be of any suitable type for use with the distillation column, for example it may be of the shell and tube heat exchanger type, such as a thermo-siphon or kettle type reboiler. Steam may be used as the heat source in the reboiler. Increasing the reboiler duty (boil-up ratio) to the column, typically by means of a temperature controller, decreases the flow rate of the water stream exiting the column. A preferred boil-up ratio is 0.01 to 5.

The water stream recovered from the crude dehydration product may be utilised to generate steam, re-utilised within the present process or other processes and/or discarded from the process as a waste effluent.

Suitably, the water stream recovered from the crude dehydration product is withdrawn from a distillation column as a base stream, typically as a liquid.

A dimethyl ether stream comprising dimethyl ether and methanol may be recovered as a heads stream from the distillation column. Typically, the dimethyl ether stream also comprises some water. The exact composition of the heads stream will vary depending on the composition of the feed and the desired amount of water to be removed in the water stream from the column. The more water removed from the column, the richer the heads stream will become in dimethyl ether and methanol. In general, however distillation of the dehydration product results in a dimethyl ether stream which comprises mainly dimethyl ether together with smaller amounts of methanol and water. Desirably, a dimethyl ether stream comprises >0 to 60 mol %, such as 5 to 40 mol % methanol and >0 to 60 mol %, for example >0 to 40 mol % water and balance dimethyl ether, for example 40 to 90 mol % dimethyl ether.

Typically, a dimethyl ether stream withdrawn from a distillation column as a heads product is withdrawn as a vapour. However, if desired, a dimethyl ether stream may additionally or alternatively be withdrawn from the distillation column as a liquid.

Suitably, separation of dimethyl ether from a recovered dimethyl ether stream comprising dimethyl ether, water and methanol is implemented by distillation methods.

In some or all embodiments of the present invention, dimethyl ether may be separated from a recovered dimethyl ether stream or a part thereof by distillation methods, for example by fractional distillation, in one or more distillation columns. Preference is given to a distillation method in which one or more distillation columns, preferably one distillation column, is employed. If one column is employed, it has at least 5, such as at least 15 theoretical stages, such as at least 20 theoretical stages, for example 20 to 40 theoretical stages.

Suitably, a distillation column for recovery of dimethyl ether from a dimethyl ether stream is operated at elevated pressure, such as at a pressure of about 0.5 barg (50 kPa) or more, such as about 0.5 barg to 30 barg (50 to 3000 kPa), for example about 10 to 30 barg (1000 to 30001 kPa).

In one or more embodiments, the distillation column for recovery of dimethyl ether from the dimethyl ether stream has 20 theoretical stages or thereabouts and is generally operated at a pressure of about 0.5 barg (50 kPa) or more, such as about 0.5 barg to 30 barg (50 to 3000 kPa), for example about 10 to 30 barg (1000 to 3000 kPa).

In one or more embodiments, the distillation column for recovery of dimethyl ether from the dimethyl ether stream is operated at a pressure of about 10 to 30 barg (1000 to 3000 kPa) and at a heads temperature of about 40 to 90° C.

The dimethyl ether stream may be introduced into the column as vapour or as a liquid.

Preferably, dimethyl ether is recovered from a dimethyl ether stream comprising dimethyl ether and methanol by distillation in a distillation column wherein (i) dimethyl ether is recovered as a heads product from the distillation column;

(ii) a methanol stream comprising methanol and water is recovered as a base stream from the distillation column.

Typically, the majority of dimethyl ether present in the dimethyl ether feed to the distillation column is removed as a heads product from the column. The heads product may be removed as a liquid or as a vapour, preferably as a liquid. Recovered dimethyl ether may be supplied to processes which require dimethyl ether as a starting material or in another function.

Suitably, a methanol stream removed from the distillation column comprises methanol and water and it may also comprise some dimethyl ether. In general, the methanol stream may have a dimethyl ether content of 3 mol % or less, for example 0 to 2 mol %.

Suitably, the distillation column is operated with a return of liquid reflux to the head of the column at a reflux to overhead ratio dependent upon such factors as the required overhead stream composition. A suitable reflux ratio may be in the range 1 to 10, for example 1.5 to 2.5. A suitable boil-up ratio may be 0.01 to 5.

In preferred embodiments of the present invention, one or more methyl acetate-rich streams, either as fresh or as recycle streams, is introduced into the distillation column and methyl acetate is recovered from the column as a component of the methanol stream. Desirably, methyl acetate-rich feeds introduced into the distillation column comprise mainly methyl acetate, preferably in an amount of at least 50 mol %. A methyl acetate feed to the distillation column may be introduced into the column as a liquid or a vapour or a mixture thereof.

Methyl acetate for supply to the distillation column may be recovered from processes for the carbonylation of dimethyl ether with carbon monoxide in the presence of a carbonylation catalyst, preferably a zeolite catalyst such as mordenite and preferably in the presence of hydrogen. Such processes are known, for example from U.S. Pat. No. 7,465,822, WO 2008/132438 and WO 2008/132468.

Typically, methyl acetate streams recovered from such carbonylation processes comprise mainly methyl acetate and may also comprise additional components such as one or more of unreacted dimethyl ether, methanol and water. In general, a methyl acetate stream may comprise dimethyl ether in an amount of 50 mol % or less, for example of about 5 to 45 mol %. Typically, a methyl acetate stream might comprise 50 to 95 mol % methyl acetate and 5 to 45 mol % dimethyl ether.

Contaminants such as one or both of acetaldehyde and methyl formate may be generated via side-reactions occurring in one or both of methanol synthesis and methyl acetate production processes. Advantageously, such contaminants present in one or more of methyl acetate and methanol containing feeds to the distillation column for recovery of dimethyl ether may be conveniently removed from the column as a sidedraw stream Suitably, the sidedraw stream is withdrawn from the distillation column at a point above the base of the column and at or above the introduction of the feed(s) to the column. Preferably, the sidedraw stream is withdrawn from the distillation column as a liquid.

Recovery of contaminants as a sidedraw stream from the column can be enhanced by providing sufficient stripping capacity in the distillation column below the feed point(s) to the column. Suitably, the distillation column has at least 3 theoretical stages, for example 3 to 33, such as 3 to 10 theoretical stages, below the feed point of a dimethyl ether feed to the column.

The first used methanol stream comprises methanol and methyl acetate and may also comprise one or more of water and dimethyl ether.

In a preferred embodiment of the present invention, the first used methanol stream or a portion thereof is combined with a methyl acetate-containing stream recovered from a carbonylation process, preferably comprising principally methyl acetate and the combined stream is distilled in a distillation column together with one or more of the dimethyl ether streams recovered from one or both of the crude dehydration product or the dehydration-hydrolysis reaction product, to recover from the column dimethyl ether, suitably as an overhead stream and a methanol stream comprising methanol, water and methyl acetate, suitably as a base stream from the column.

Alternatively, the first used methanol stream or a portion thereof, the methyl acetate-containing stream from carbonylation and one or more dimethyl ether streams recovered from one or both of the crude dehydration product and dehydration-hydrolysis reaction product can be supplied to a distillation column as separate feeds and distilled therein to recover from the column dimethyl ether, suitably as an overhead stream and a methanol stream comprising methanol, water and methyl acetate, suitably as a base stream from the column.

In preferred embodiments of the present invention, for a distillation column having 20 to 40 theoretical stages, the methyl acetate feed point may be at stage 10 to 25 counted from the head, the dimethyl ether feed point may be at stage 5 to 25 from the head and a sidedraw stream may be withdrawn, preferably as a liquid, at stages 4 to 15 from the head and at or above the dimethyl ether and methyl acetate feed points to the column.

The methanol stream, or a portion thereof, comprising methanol and water, and optionally and preferably methyl acetate, is supplied as a feed to the dehydration-hydrolysis reaction step. Desirably, the total amount of acetaldehyde and methyl formate contaminants present in the methanol feed stream is 1 mol % or less.

Typically, methanol is produced commercially by converting a mixture of carbon monoxide, hydrogen and carbon dioxide in the presence of a catalyst according to the overall equation $CO+2H_2 \rightleftharpoons CH_3OH$. The reaction proceeds in accordance with the following equations:

$$CO_2 + 3H_2 \rightleftharpoons CH_3OH + H_2O \quad \text{(I)}$$

$$H_2O + CO \rightleftharpoons CO_2 + H_2 \quad \text{(II)}$$

Methanol for use in the process of the present invention may be obtained directly from such synthesis processes or imported methanol from other suitable sources such as that stored in conventional methanol storage tanks. Preferably, however the first and second portions of methanol are provided from a methanol synthesis process which synthesis process is integrated with the processes as described herein.

Thus, the present invention yet further provides an integrated process for the co-production of acetic acid and dimethyl ether by the dehydration-hydrolysis of methanol and methyl acetate which process comprises:

contacting a gaseous mixture of carbon monoxide, hydrogen and preferably carbon dioxide in the presence of a methanol synthesis catalyst to produce methanol;

contacting a gaseous mixture of carbon monoxide, hydrogen, and methyl acetate contaminant and optionally carbon dioxide in a first scrubbing zone with a first portion of the methanol to recover a scrubbed gaseous mixture depleted in methyl acetate and a first used methanol stream containing methyl acetate;

contacting the scrubbed gaseous mixture in a second scrubbing zone with a second portion of the methanol to recover a scrubbed gaseous mixture further depleted in methyl acetate and a second used methanol stream containing a reduced amount of methyl acetate compared to the first used methanol stream; and dehydrating at least a portion of the second used methanol stream in the presence of at least one catalyst to produce a crude dehydration reaction product comprising dimethyl ether, unconverted methanol, water and acetic acid recovering from the crude dehydration product a water stream comprising mainly water and 3 mol % or less acetic acid and a dimethyl ether stream comprising dimethyl ether, and methanol;

separating dimethyl ether from the dimethyl ether stream to produce a methanol stream comprising methanol and water; and contacting the methanol stream or a part thereof, methyl acetate and optionally one or more recycle streams comprising one or more of methanol, methyl acetate and water in the presence of at least one catalyst to generate a dehydration-hydrolysis reaction product comprising dimethyl ether and acetic acid.

In one or all embodiments of the present invention, the first and second portions of methanol are provided by methanol produced from a methanol synthesis process in which synthesis process a gaseous reactant mixture of carbon monoxide, hydrogen and carbon dioxide is fed to a methanol synthesis reactor and contacted therein in the presence of a methanol synthesis catalyst to produce a methanol product which methanol product is withdrawn from the methanol synthesis reactor. In addition to methanol, the methanol product may comprise one or more of dimethyl ether, carbon monoxide, carbon dioxide, hydrogen and water. The methanol product produced may be treated by conventional purification means, for example by gas/liquid separation techniques, to recover a liquid purified methanol product stream which methanol stream or a part thereof is subsequently supplied, optionally via one or more heat exchangers, to the first and second scrubbing zones and utilised therein to scrub a gaseous mixture of carbon monoxide, hydrogen and methyl acetate contaminant. Alternatively, the methanol product or part thereof produced from the synthesis process is liquefied, for example using one or more condensing means, to provide a liquid methanol product stream, which liquid methanol stream provides the first and second portions of methanol for use in the first and second scrubbing zones. Preferably, in these embodiments, the liquid methanol product stream is split so as to provide a ratio of the amount of the first portion of methanol to the amount of the second portion in the range 1:5 to 1:15, for example 1:10. Preferably, in these embodiments, the methanol synthesis process forms an integrated process with the scrubbing processes as described herein. Preferably, the integrated methanol synthesis process provides all of the methanol required for use in the first and second scrubbing zones. However, if desired, a quantity of imported methanol may additionally be utilised therein.

In general, a gaseous feed mixture for methanol synthesis comprises carbon monoxide, hydrogen and carbon dioxide. The stoichiometric number ("SN") of a gaseous mixture comprising carbon monoxide, hydrogen and carbon dioxide is conventionally calculated as $SN=(H_2-CO_2)/(CO+CO_2)$ wherein $H_2$, $CO$ and $CO_2$ represent the composition of the gas on a molar basis. Desirably, the SN of a gaseous mixture for methanol synthesis is from 1.5 to 2.5, preferably from 2.0 to 2.1.

Scrubbing of gaseous mixtures comprising carbon monoxide, hydrogen and optionally carbon dioxide with pure methanol does not alter substantially the amounts of carbon monoxide, hydrogen or carbon dioxide present in such mixtures. However, if one or more of carbon monoxide, hydrogen and carbon dioxide are present in the scrubbing methanol a portion of these components may be released from the methanol during scrubbing and form part of the recovered scrubbed gaseous mixture. In general however, the stoichiometric number of a gaseous mixture contacted with the second portion of methanol in the second scrubbing zone corresponds approximately to the stoichiometric number of the gaseous mixture prior to contact with the first portion of methanol.

In one or more embodiments of the present invention, the scrubbed gaseous mixture or a part thereof recovered from the second scrubbing zone is supplied as a feed to a methanol synthesis process. In these embodiments, it is preferred that the scrubbed gaseous mixture comprises methyl acetate in an amount of 0 to 0.1 mol % and more preferably further comprises carbon dioxide. If desired, one of more additional carbon dioxide and synthesis gas may be supplied to a methanol synthesis process as separate feeds to or together with the scrubbed gaseous mixture. Desirably, the SN of the scrubbed gaseous mixture recovered from the second scrubbing zone together with any additional fresh syngas or carbon dioxide feeds and supplied to a methanol synthesis process is from 1.5 to 2.5, preferably from 2.0 to 2.1.

Methanol synthesis is usually carried out in the presence of a catalyst. A number of catalysts active for methanol synthesis are known in the art and are also available commercially. Typically, such methanol synthesis catalysts comprise copper as an active catalytic component and may also contain one or more additional metals such as zinc, magnesium and aluminium. Examples of methanol synthesis catalysts include but are not limited to catalysts comprising zinc oxide and alumina as the support with copper as the active catalytic component.

A methanol synthesis catalyst may be employed in a fixed bed, for example in the shape of pipes or tubes, wherein the mixture of carbon monoxide and hydrogen and optionally carbon dioxide is passed over or through the catalyst.

In general, methanol synthesis is carried out at a temperature of from 210° C. to 300° C. and at a total pressure of from 25 to 150 barg (2500 to 15,000 kPa).

In some or all embodiments of the present invention, a gaseous mixture of carbon monoxide and hydrogen and carbon dioxide is contacted in the presence of a methanol synthesis catalyst comprising copper as an active catalytic component to produce a methanol product comprising water and dimethyl ether. Suitably, the methanol product comprises water and dimethyl ether in a total amount of >0 to 35 mol %, for example in a total amount of >0 to 20 mol %. One or more of, carbon monoxide, carbon dioxide and hydrogen may also be components of the produced methanol.

The co-production of acetic acid and dimethyl ether by the hydrolysis of methyl acetate to produce acetic acid and dehydration of methanol to produce dimethyl ether can be represented by equations (1) and (2) respectively:

$$CH_3COOCH_3 + H_2O \rightleftharpoons CH_3COOH + CH_3OH \quad (1)$$

$$2CH_3OH \rightleftharpoons CH_3OCH_3 + H_2O \quad (2)$$

In the process of the present invention, methanol feedstock for the co-production process is obtained, for example by distilling dimethyl ether streams comprising dimethyl ether and methanol recovered from crude dehydration product streams. Typically, such distillations produce methanol as a component of the base stream. Such methanol-containing streams may be utilised as the methanol feedstock to the co-production process.

If desired, distillation of dimethyl ether streams comprising methanol, for example dimethyl ether streams recovered from distillation of the crude dehydration product or dimethyl streams recovered from the co-production process may be distilled together with methyl acetate-containing streams, for example methyl acetate-containing streams comprising methyl acetate and one or more of dimethyl ether, water and methanol. In such cases, methanol and also methyl acetate are likely to be components of a base stream from the column. Such base streams or a part thereof and comprising both methanol and methyl acetate may be supplied as a combined methanol and methyl acetate feed stream to the dehydration-hydrolysis co-production process. Alternatively and/or additionally one or more separate feed streams of methyl acetate can be supplied as to the dehydration-hydrolysis process.

Depending on the exact composition of a base stream comprising methanol and optionally methyl acetate, recovered from distillation, it may be desirable to supply additional methanol, methyl acetate and/or water to the dehydration-hydrolysis process.

The hydrolysis of methyl acetate to form acetic acid requires water as a reactant. This water may be generated in-situ via the dehydration reaction. To mitigate fluctuations or imbalances of water concentration in one or both of the methanol and methyl acetate feeds to the dehydration-hydrolysis process, the water concentration in the feeds to the process, including any recycles, may be analysed, on a periodic or continuous basis, for example by gas chromatography and if desired, the quantity of water supplied to the co-production process may be controlled. As discussed above, the quantity of water present in feeds to the dehydration-hydrolysis process can be controlled or adjusted by utilising a methanol dehydration process in accordance with the present invention, that is, wherein used scrubbing methanol from the scrubbing of mixtures of carbon monoxide, hydrogen and methyl acetate contaminant is subject to a dehydration process to generate a crude dehydration product comprising dimethyl ether, methanol and water, which crude dehydration product may be distilled, preferably by fractional distillation, in a distillation column equipped with a reboiler. The quantity of water removed during distillation is adjusted by regulating one or both of the reflux ratio and reboiler duty (boil-up ratio) to the column to increase or decrease the amount of water present in the water stream recovered from the distillation column and hence from the process.

Suitably, water is introduced into the dehydration-hydrolysis process in an amount of from about 0.1 to about 50 mol %, preferably about 5 to about 30 mol %, for example about 20 to 30 mol %, based on the total feed of methyl acetate, water and methanol to the process.

The molar ratio of methanol to methyl acetate usefully employed in the dehydration-hydrolysis process may be any desired ratio, but suitably the molar ratio of methanol:methyl acetate is in the range 1:0.1 to 1:20.

One or more catalysts may be utilised in the dehydration-hydrolysis process. Any suitable catalyst or catalysts may be used provided that it/they are effective to catalyse the hydrolysis of methyl acetate to produce acetic acid and are also effective to catalyse the dehydration of methanol to form dimethyl ether. One or more catalysts may be employed which are effective to catalyse both the hydrolysis and dehydration reactions. Alternatively, one or more catalysts effective for catalysing the hydrolysis may be used in addition to or as an admixture with one or more catalysts for the dehydration reaction. Where it is desired to employ two or more different catalysts, such catalysts may be utilised in the form of alternating catalyst beds or as one or more intimately mixed catalyst beds.

Preferably, one or more solid acid catalysts are utilised in the dehydration-hydrolysis process, such as one or more solid Brønsted acid catalysts. Solid acid catalysts useful for the dehydration of methanol to produce dimethyl ether include one or more of the catalysts, as herein described above, which can be utilised in the dehydration of the second used methanol stream to form dimethyl ether.

Zeolites known to be effective for the hydrolysis of methyl acetate to produce acetic acid include zeolite Y, zeolite A, zeolite X and mordenite zeolite. If desired, these zeolites can be usefully employed as a catalyst in the dehydration-hydrolysis reaction step of the present invention.

Particularly useful zeolite catalysts for use in the dehydration-hydrolysis process include zeolites having a 2-dimensional or 3 dimensional channel system and at least one channel of which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

A zeolite catalyst may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For use in the dehydration-hydrolysis process, the zeolite may be in an exchanged form with one or more alkali metal cations such as sodium, lithium, potassium and cesium cations. Suitable exchanged form zeolites include ferrierite and ZSM-35 exchanged with one or more of sodium, lithium, potassium and cesium.

A zeolite may be used in the form of a composite with any suitable binder material.

Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

The dehydration-hydrolysis process may be carried out as a heterogeneous vapour phase process or as a liquid phase process. If it is desired to conduct the process as a vapour phase process, it is preferable to volatilise liquid feed(s), for example in a pre-heater prior to contact with the catalyst.

The dehydration-hydrolysis process may be carried out at temperatures in the range of about 100° C. to 350° C. and at atmospheric pressure or pressures greater than atmospheric.

In one or more embodiments of the present invention, the dehydration-hydrolysis process is conducted as a vapour phase process at a temperature of about 150° C. to 350° C. and a pressure of atmospheric to 30 barg (atmospheric to 3000 kPa), for example 5 to 20 barg (500 kPa to 2000 kPa).

Suitably, in such cases, dehydration-hydrolysis is carried out at a gas hourly space velocity (GHSV) in the range 500 to 40,000 h$^{-1}$.

In one or more embodiments of the present invention, the dehydration-hydrolysis is conducted as a liquid phase process and is carried out at temperatures of from about 140° C. to about 210° C. and at a pressure which is sufficient to maintain dimethyl ether product in solution, such as pressures of 40 barg (4000 kPa) or higher, for example 40 to 100 barg (4000 to 10,000 kPa). Suitably, in such cases, dehydration-hydrolysis is carried out at a liquid hourly space velocity (LHSV) in the range 0.2 to 20 h$^{-1}$.

In the present invention, the dehydration-hydrolysis process may be carried out using any suitable technique and apparatus, for example by reactive distillation. Reactive distillation techniques and apparatus therefor are well-known. In such reactive distillation processes, the feed stocks, that is the methanol feed comprising methanol and water combined with or separate from a methyl acetate feed, may be supplied to a conventional reactive distillation column, operated at, for example a pressure in the range atmospheric to 20 barg (atmospheric to 2000 kPa) and at a reaction temperature of about 100° C. to 350° C., to produce a crude reaction product comprising a mixture of acetic acid and dimethyl ether which mixture is inherently separated within the reactive distillation column to recover a product stream rich in dimethyl ether, typically recovered as an overhead from the column, and a product stream rich in acetic acid, typically recovered as a base stream from the column.

Alternatively, the dehydration-hydrolysis process may be carried out in a fixed bed reactor or a slurry bed reactor. Dimethyl ether has a low boiling point (−24° C.) and acetic acid has a high boiling point (118° C.). Thus, acetic acid and dimethyl ether present in the dehydration-hydrolysis reaction product may be recovered therefrom by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as an overhead from the distillation column, and a stream rich in acetic acid is recovered as a base stream from the column.

One or both of the dimethyl ether-rich and acetic acid-rich streams may comprise additional components such as one or more of methanol, methyl acetate and water. These components can be removed by conventional purification processes, such as by distillation of the dimethyl ether-rich and/or acetic acid-rich stream in one or more distillation columns to recover purified dimethyl ether and/or purified acetic acid streams and streams comprising one or more of methanol, methyl acetate and water which may be utilised as recycle streams.

Suitably, one or more recycle streams are returned to the dehydration-hydrolysis process comprising one or more of methanol, methyl acetate and water.

The co-production process may be operated as a continuous process or as a batch process, preferably as a continuous process.

Dimethyl ether may be sold or used as a fuel or as a feedstock to chemical processes, such as carbonylation processes to produce carboxylic acids and/or carboxylic acid esters.

Acetic acid may be sold or may be used as a feedstock in a variety of chemical processes, such as the manufacture of vinyl acetate or ethyl acetate.

The invention is now illustrated with reference to the following non-limiting Examples.

EXAMPLE 1

This Example demonstrates a process for the co-production of acetic acid and dimethyl ether in which the purity of a waste water stream, and in particular the acetic acid content of a waste water stream, is controlled in accordance with the present invention. Reference is made to the drawing and Table 1. The drawing illustrates schematically an integrated unit (110) for carrying out embodiments of the process of the present invention. The unit (110) incorporates a first and second scrubbing zones (111) and (113) each zone containing 5 stages and operated at a pressure of 74 barg and a temperature of about 50° C. A gaseous stream (11) comprising a mixture of carbon monoxide, hydrogen and methyl acetate such as that derived from a process for the carbonylation of dimethyl ether with carbon monoxide in the presence of a catalyst, such as a zeolite catalyst, hydrogen and carbon dioxide (carbonylation process not shown) is passed to a first scrubbing zone (111) and contacted countercurrently with a first portion of methanol scrubbing solvent (42) supplied from methanol splitter unit (112); methanol splitter unit (112) is supplied with fresh methanol such as that synthesised in a methanol production unit (not shown) via stream (14). A used methanol stream containing absorbed methyl acetate is removed from the first scrubbing zone (111) as stream (40). A stream (18) of scrubbed gaseous mixture having a reduced methyl acetate content is directly passed from the first scrubbing zone (111) to a second scrubbing zone (113) where it is contacted with a countercurrent flow of a second portion of methanol (41) supplied from methanol splitter unit (112). The scrubbed gaseous mixture further depleted in methyl acetate is removed from the second scrubbing zone (113) as stream (37). A used methanol stream (39) comprising methanol, water, dimethyl ether and less than 0.1 mol % methyl acetate is removed from the second scrubbing zone (113) and introduced into a dehydration reactor (114) containing a dehydration catalyst, suitably a solid acid catalyst, suitably a zeolite catalyst. Suitably, dehydration reactor (114) is maintained under conditions of 100 to 350° C., preferably 150 to 300° C. and at a pressure of 10 to 20 barg. In dehydration reactor (114) methanol is dehydrated in the presence of the catalyst to produce a crude dehydration product stream (10) comprising dimethyl ether, water and unreacted methanol which is withdrawn from reactor (114), cooled in heat exchanger (115) and subsequently introduced into distillation 30 column (116) equipped with a reboiler. Distillation column (116) has 15 theoretical stages with feed of the crude dehydration product onto stage 10 (counted from the head of the column) and is operated at 13.5 barg and a heads temperature of 146° C., a base temperature of 176° C., a reflux ratio of 0.3 and a boil-up ratio of 0.025. A waste water stream (9) comprising mainly water and less than 0.1 mol % acetic acid is removed as a base stream from column (116). A stream (8) comprising dimethyl ether, methanol and water is removed from column (116) as a heads stream. Dimethyl ether stream (8) is passed to distillation column (117) equipped with a reboiler. Distillation column (117) has 20 theoretical stages with the feed point of the dimethyl ether stream (8) at stage 10 of the column (counted from the head of the column) and is operated at 11.7 barg, a heads temperature of 45° C., a base temperature of 162° C., a reflux ratio of 2.0 and a boil-up ratio of 0.19. Dimethyl ether is withdrawn from the distillation column (117) as heads stream (12). A vent stream (43) comprising mainly carbon oxides and hydrogen is also withdrawn from column (117). A stream (13) comprising methanol and water is withdrawn as a base stream from column (117). Stream (13) and a methyl acetate stream (17) are mixed in mixer (118), for example a T-piece mixer, and the mixed stream (15) is supplied to dehydration-hydrolysis reactor (119), such as a fixed bed reactor. In reactor (119) stream (15) is contacted with at least one solid acid catalyst, for example a heteropolyacid or zeolite catalyst, at elevated pressure and a temperature of 100 to 350° C. to generate a reaction product comprising acetic acid and dimethyl ether which is withdrawn from reactor (119) as product stream (16).

Utilising the procedure and apparatus of the type illustrated in the drawing, simulations were carried out using ASPEN software version 7.3. The compositions of the streams (in units kmol/hr and mol %) in this Example are shown in Table 1 in which the following abbreviations are used:

CO—carbon monoxide
$CO_2$—carbon dioxide
$H_2$—hydrogen
MeOH—methanol
AcOH—acetic acid
DME—dimethyl ether
MeOAc—methyl acetate

EXAMPLE 2

This Example illustrates control of water flow to acetic acid and dimethyl ether production in accordance with embodiments of the process of the present invention. Example 1 was repeated using the apparatus and flow scheme illustrated in the drawing except that the reflux ratio and boil-up ratio of distillation column (116) were adjusted to have the following values; reflux ratio of 0.25 and boil-up ratio of 1.5. The compositions of the streams (in units kmol/hr and mol %) in this Example 2 are shown in Table 2 in which the following abbreviations are used:

CO—carbon monoxide
$CO_2$—carbon dioxide
$H_2$—hydrogen
MeOH—methanol
AcOH—acetic acid
DME—dimethyl ether
MeOAc—methyl acetate

TABLE 1

| Stream mol flow | 11 | | 14 | | 41 | | 42 | | 40 | | 18 | | 37 | |
|---|---|---|---|---|---|---|---|---|---|---|---|---|---|---|
| | | | | | | | | | mol % | | | | | |
| CO | 550.0 | 22.0 | 0.0 | 0.0 | 0.0 | 0.0 | 0.0 | 0.0 | 2.7 | 1.1 | 547.3 | 23.2 | 542.6 | 23.7 |
| $CO_2$ | 100.0 | 4.0 | 0.0 | 0.0 | 0.0 | 0.0 | 0.0 | 0.0 | 7.0 | 2.8 | 93.0 | 3.9 | 84.1 | 3.7 |
| $H_2$ | 1625.0 | 65.0 | 0.0 | 0.0 | 0.0 | 0.0 | 0.0 | 0.0 | 4.3 | 1.7 | 1620.7 | 68.7 | 1610.6 | 70.4 |
| MeOH | 0.0 | 0.0 | 979.0 | 89.0 | 881.1 | 89.0 | 97.9 | 89.0 | 75.9 | 30.1 | 22.0 | 0.9 | 22.3 | 1.0 |
| AcOH | 0.0 | 0.0 | 0.0 | 0.0 | 0.0 | 0.0 | 0.0 | 0.0 | 0.0 | 0.0 | 0.0 | 0.0 | 0.0 | 0.0 |
| Water | 0.0 | 0.0 | 99.0 | 9.0 | 89.1 | 9.9 | 9.9 | 9.0 | 8.9 | 3.5 | 1.0 | 0.0 | 0.9 | 0.0 |
| DME | 125.0 | 5.0 | 22.0 | 2.0 | 19.8 | 2.0 | 2.2 | 2.0 | 54.3 | 21.5 | 72.9 | 3.1 | 27.9 | 1.2 |
| MeOAc | 100.0 | 4.0 | 0.0 | 0.0 | 0.0 | 0.0 | 0.0 | 0.0 | 99.1 | 39.3 | 0.9 | 363 ppm | 0.0 | 0.007 ppm |

| Stream mol flow | 39 | | 10 | | 9 | | 8 | |
|---|---|---|---|---|---|---|---|---|
| | | | mol % | | | | | |
| CO | 4.7 | 0.4 | 4.7 | 0.4 | 0.0 | 0.0 | 4.7 | 0.6 |
| $CO_2$ | 8.8 | 0.8 | 8.8 | 0.8 | 0.0 | 0.0 | 8.8 | 1.1 |
| $H_2$ | 10.1 | 1.0 | 10.1 | 1.0 | 0.0 | 0.0 | 10.1 | 1.2 |
| MeOH | 880.8 | 83.2 | 127.7 | 12.1 | 12.0 | 5.0 | 115.7 | 14.2 |
| AcOH | 0.0 | 0.0 | 0.1 | 0.0 | 0.1 | 0.1 | 0.0 | 0.0 |
| Water | 89.1 | 8.4 | 465.6 | 44.0 | 228.5 | 94.2 | 237.1 | 29.0 |
| DME | 64.9 | 6.1 | 441.5 | 41.7 | 1.8 | 0.7 | 439.7 | 53.8 |
| MeOAc | 0.9 | 0.08 | 0.7 | 0.07 | 0.0 | 0.0 | 0.7 | 0.1 |

| Stream mol flow | 43 | | 12 | | 13 | | 17 | | 15 | | 16 | |
|---|---|---|---|---|---|---|---|---|---|---|---|---|
| | | | | | mol % | | | | | | | |
| CO | 4.5 | 4.3 | 0.2 | 0.1 | 0.0 | 0.0 | 0.0 | 0.0 | 0.0 | 0.0 | 0.0 | 0.0 |
| CO2 | 5.2 | 4.9 | 3.7 | 1.0 | 0.0 | 0.0 | 0.0 | 0.0 | 0.0 | 0.0 | 0.0 | 0.0 |
| $H_2$ | 9.8 | 9.4 | 0.3 | 0.1 | 0.0 | 0.0 | 0.0 | 0.0 | 0.0 | 0.0 | 0.0 | 0.0 |
| MeOH | 0.0 | 0.0 | 0.2 | 0.0 | 115.5 | 32.7 | 0.0 | 0.0 | 115.5 | 8.5 | 43.1 | 3.2 |
| AcOH | 0.0 | 0.0 | 0.0 | 0.0 | 0.0 | 0.0 | 0.0 | 0.0 | 0.0 | 0.0 | 171.6 | 12.7 |
| Water | 0.0 | 0.0 | 0.0 | 0.0 | 237.1 | 67.0 | 0.0 | 0.0 | 237.1 | 17.5 | 187.6 | 13.9 |
| DME | 85.2 | 81.4 | 354.2 | 98.8 | 0.4 | 0.1 | 0.0 | 0.0 | 0.4 | 0.0 | 122.4 | 9.0 |
| MeOAc | 0.0 | 0.0 | 0.0 | 0.0 | 0.7 | 0.2 | 1000.0 | 100.0 | 1000.7 | 73.9 | 829.1 | 61.2 |

TABLE 2

| Stream mol flow | 11 | | 14 | | 41 | | 42 | | 40 | | 18 | | 37 | |
|---|---|---|---|---|---|---|---|---|---|---|---|---|---|---|
| | | | | | | | mol % | | | | | | | |
| CO | 550.0 | 22.0 | 0.0 | 0.0 | 0.0 | 0.0 | 0.0 | 0.0 | 2.7 | 1.1 | 547.3 | 23.2 | 542.6 | 23.7 |
| $CO_2$ | 100.0 | 4.0 | 0.0 | 0.0 | 0.0 | 0.0 | 0.0 | 0.0 | 7.0 | 2.8 | 93.0 | 3.9 | 84.1 | 3.7 |
| $H_2$ | 1625.0 | 65.0 | 0.0 | 0.0 | 0.0 | 0.0 | 0.0 | 0.0 | 4.3 | 1.7 | 1620.7 | 68.7 | 1610.6 | 70.4 |
| MeOH | 0.0 | 0.0 | 979.0 | 89.0 | 881.1 | 89.0 | 97.9 | 89.0 | 75.9 | 30.1 | 22.0 | 0.9 | 22.3 | 1.0 |
| AcOH | 0.0 | 0.0 | 0.0 | 0.0 | 0.0 | 0.0 | 0.0 | 0.0 | 0.0 | 0.0 | 0.0 | 0.0 | 0.0 | 0.0 |
| Water | 0.0 | 0.0 | 99.0 | 9.0 | 89.1 | 9.0 | 9.9 | 9.0 | 8.9 | 3.5 | 1.0 | 0.0 | 0.9 | 0.0 |
| DME | 125.0 | 5.0 | 22.0 | 2.0 | 19.8 | 2.0 | 2.2 | 2.0 | 54.3 | 21.5 | 72.9 | 3.1 | 27.9 | 1.2 |
| MeOAc | 100.0 | 4.0 | 0.0 | 0.0 | 0.0 | 0.0 | 0.0 | 0.0 | 99.1 | 39.3 | 0.9 | 363 ppm | 0.0 | 0.007 ppm |

| Stream mol flow | 39 | | 10 | | 9 | | 8 | |
|---|---|---|---|---|---|---|---|---|
| | | | mol % | | | | | |
| CO | 4.7 | 0.4 | 4.7 | 0.4 | 0.0 | 0.0 | 4.7 | 0.5 |
| $CO_2$ | 8.8 | 0.8 | 8.8 | 0.8 | 0.0 | 0.0 | 8.8 | 0.9 |
| $H_2$ | 10.1 | 1.0 | 10.1 | 1.0 | 0.0 | 0.0 | 10.1 | 1.1 |
| MeOH | 880.8 | 83.2 | 127.7 | 12.1 | 0.0 | 0.0 | 127.7 | 13.4 |
| AcOH | 0.0 | 0.0 | 0.14 | 0.01 | 0.09 | 0.09 | 0.1 | 0.0 |
| Water | 89.1 | 8.4 | 465.6 | 44.0 | 102.5 | 99.9 | 363.1 | 38.0 |
| DME | 64.9 | 6.1 | 441.5 | 41.7 | 0.0 | 0.0 | 441.5 | 46.1 |
| MeOAc | 0.9 | 0.08 | 0.7 | 0.07 | 0.0 | 0.0 | 0.7 | 0.1 |

| Stream mol flow | 43 | | 12 | | 13 | | 17 | | 15 | | 16 | |
|---|---|---|---|---|---|---|---|---|---|---|---|---|
| | | | | | mol % | | | | | | | |
| CO | 4.5 | 4.3 | 0.2 | 0.1 | 0.0 | 0.0 | 0.0 | 0.0 | 0.0 | 0.0 | 0.0 | 0.0 |
| $CO_2$ | 5.1 | 4.9 | 3.7 | 1.0 | 0.0 | 0.0 | 0.0 | 0.0 | 0.0 | 0.0 | 0.0 | 0.0 |
| $H_2$ | 9.8 | 9.4 | 0.3 | 0.1 | 0.0 | 0.0 | 0.0 | 0.0 | 0.0 | 0.0 | 0.0 | 0.0 |
| MeOH | 0.0 | 0.0 | 0.2 | 0.0 | 127.5 | 25.9 | 0.0 | 0.0 | 127.5 | 8.5 | 57.6 | 3.9 |
| AcOH | 0.0 | 0.0 | 0.0 | 0.0 | 0.1 | 0.0 | 0.0 | 0.0 | 0.1 | 0.0 | 206.0 | 13.8 |
| Water | 0.0 | 0.0 | 0.0 | 0.0 | 363.1 | 73.8 | 0.0 | 0.0 | 363.1 | 24.3 | 295.1 | 19.8 |
| DME | 85.1 | 81.4 | 355.9 | 98.8 | 0.5 | 0.1 | 0.0 | 0.0 | 0.5 | 0.0 | 138.4 | 9.3 |
| MeOAc | 0.0 | 0.0 | 0.0 | 0.0 | 0.7 | 0.1 | 1000.0 | 100.0 | 1000.7 | 67.1 | 794.8 | 53.3 |

The invention claimed is:

1. A process for the production of dimethyl ether from gaseous mixtures of carbon monoxide, hydrogen and methyl acetate contaminant which process comprises:

contacting a gaseous mixture of carbon monoxide, hydrogen and methyl acetate contaminant in a first scrubbing zone with a first portion of methanol to recover a scrubbed gaseous mixture depleted in methyl acetate and a first used methanol stream containing methyl acetate;

contacting the scrubbed gaseous mixture in a second scrubbing zone with a second portion of methanol to recover a scrubbed gaseous mixture further depleted in methyl acetate and a second used methanol stream containing no methyl acetate or a reduced amount of methyl acetate compared to the first used methanol stream;

dehydrating at least a portion of the second used methanol stream in the presence of at least one catalyst to produce a crude dehydration reaction product comprising dimethyl ether, unconverted methanol and water;

recovering from the crude dehydration product a water stream comprising water and 3 mol % or less acetic acid and a dimethyl ether stream.

2. A process for the co-production of acetic acid and dimethyl ether by dehydration-hydrolysis of methanol and methyl acetate which process comprises:

contacting a gaseous mixture of carbon monoxide, hydrogen and methyl acetate contaminant in a first scrubbing zone with a first portion of methanol to recover a scrubbed gaseous mixture depleted in methyl acetate and a first used methanol stream containing methyl acetate;

contacting the scrubbed gaseous mixture in a second scrubbing zone with a second portion of methanol to recover a scrubbed gaseous mixture further depleted in methyl acetate and a second used methanol stream containing a reduced amount of methyl acetate compared to the first used methanol stream;

dehydrating at least a portion of the second used methanol stream in the presence of at least one catalyst to produce a crude dehydration reaction product comprising dimethyl ether, unconverted methanol, water and acetic acid;

recovering from the crude dehydration product a water stream comprising water and 3 mol % or less acetic acid and a dimethyl ether stream comprising dimethyl ether and methanol;

separating dimethyl ether from the dimethyl ether stream to produce a methanol stream comprising methanol and water; and contacting the methanol stream or a part thereof, methyl acetate and optionally one or more recycle streams comprising one or more of methanol, methyl acetate and water in the presence of at least one catalyst to generate a dehydration-hydrolysis reaction product comprising dimethyl ether and acetic acid.

3. A process according to claim 1 wherein the gaseous mixture provided to the first scrubbing zone comprises methyl acetate in an amount of >0 to 5 mol %.

4. A process according to claim 1 wherein the water stream recovered from the crude dehydration product comprises water in an amount of at least 95 mol % and 0 to 1 mol % acetic acid.

5. A process according to claim 1 wherein the first and second scrubbing zones are integrated within a single scrubbing column.

6. A process according to claim 1 wherein the first portion of methanol and the second portion of methanol are provided from a single methanol feed.

7. A process according to claim 6 wherein the single methanol feed is split to provide a ratio of the amount of the first portion of methanol to the amount of the second portion of methanol in the range 1:5 to 1:15.

8. A process according to claim 1 wherein the ratio of the amount of the first portion of methanol to the amount of the second portion of methanol is in the range 1:5 to 1:15.

9. A process according to claim 1 wherein the first portion of methanol removes 90 to <100 wt % methyl acetate from the gaseous mixture.

10. A process according to claim 1 wherein the second used methanol stream comprises 0 to 0.5 mol % methyl acetate.

11. A process according to claim 1 wherein dehydration of the second used methanol stream is conducted as a heterogeneous process and wherein the heterogeneous process is conducted in the vapour phase at temperatures of from 150° C. to 300° C.

12. A process according to claim 1 wherein the water stream recovered from the crude dehydration product is recovered by fractional distillation in a distillation column and the amount of water present in the water stream withdrawn from the column is controlled by adjusting one or both of the reflux ratio to the column and the reboiler duty.

13. A process according to claim 1 wherein the gaseous mixture comprising carbon monoxide, hydrogen and methyl acetate contaminant contacted with the first portion of methanol is a gaseous mixture recovered from a crude carbonylation product comprising methyl acetate, unreacted carbon monoxide and hydrogen, which crude carbonylation product is produced by carbonylating dimethyl ether with a carbon monoxide-containing gas in the presence of a carbonylation catalyst and hydrogen.

14. A process according to claim 1 wherein the first and second portions of methanol are provided by methanol produced from a methanol synthesis process in which synthesis process a gaseous reactant mixture of carbon monoxide, hydrogen and carbon dioxide is fed to a methanol synthesis reactor and contacted therein in the presence of a methanol synthesis catalyst to produce a methanol product and which methanol synthesis process forms an integrated process with the process of claim 1.

15. A process according to claim 14 wherein the gaseous mixture or a part thereof recovered from the second scrubbing zone is supplied as a feed to the methanol synthesis process.

16. A process according to claim 1 wherein the dehydration of methanol is carried out in the presence of a solid acid catalyst.

17. A process according to claim 16 wherein the solid acid catalyst is selected from aluminas, acidic zirconia, aluminium phosphate, silica-alumina supported tungsten oxides, heteropolyacids and salts thereof and aluminosilicate zeolites.

18. A process according to claim 2 wherein one or more recycle streams comprising one or more of methanol, methyl acetate and water are returned to dehydration-hydrolysis.

19. A process according to claim 2 wherein dehydration-hydrolysis is carried out at temperatures in the range 100 to 350° C. and at atmospheric pressure or pressures greater than atmospheric.

20. A process according to claim 2 wherein the co-production process is operated as a continuous process.

21. A process according to claim 2 wherein one or more of the dehydration of methanol and the dehydration of methanol and methyl acetate is carried out in the presence of a solid acid catalyst.

22. A process according to claim 21 wherein the solid catalyst is selected from aluminas, acidic zirconia, aluminium phosphate, silica-alumina supported tungsten oxides, heteropolyacids and salts thereof and aluminosilicate zeolites.

* * * * *